United States Patent
Rosing

(10) Patent No.: US 10,329,458 B2
(45) Date of Patent: Jun. 25, 2019

(54) SELECTIVELY-RELEASABLE ADHESIVES AND ARTICLES THAT INCORPORATE THEM

(71) Applicant: Global Biomedical Technologies, LLC, Naples, FL (US)

(72) Inventor: Howard Rosing, Naples, FL (US)

(73) Assignee: Global Biomedical Technologies, L.L.C., Naples, FL (US)

( * ) Notice: Subject to any disclaimer, the term of this patent is extended or adjusted under 35 U.S.C. 154(b) by 563 days.

(21) Appl. No.: 13/940,527

(22) Filed: Jul. 12, 2013

(65) Prior Publication Data

US 2014/0018718 A1    Jan. 16, 2014

Related U.S. Application Data

(60) Provisional application No. 61/671,449, filed on Jul. 13, 2012.

(51) Int. Cl.
| | |
|---|---|
| *C09J 11/06* | (2006.01) |
| *C08L 33/08* | (2006.01) |
| *A61F 13/02* | (2006.01) |
| *A61L 15/42* | (2006.01) |
| *A61L 15/50* | (2006.01) |

(Continued)

(52) U.S. Cl.
CPC .......... *C09J 11/06* (2013.01); *A61F 13/0253* (2013.01); *A61L 15/42* (2013.01); *A61L 15/50* (2013.01); *A61L 15/58* (2013.01); *C09J 7/38* (2018.01); *C09J 2201/20* (2013.01); *C09J 2205/102* (2013.01); *C09J 2433/00* (2013.01); *C09J 2475/00* (2013.01); *C09J 2483/00* (2013.01); *Y10T 428/24322* (2015.01); *Y10T 428/249983* (2015.04); *Y10T 428/2804* (2015.01); *Y10T 428/2852* (2015.01); *Y10T 428/2891* (2015.01); *Y10T 442/2738* (2015.04)

(58) Field of Classification Search
CPC .............. A61F 2013/0017; A61F 13/02; A61F 13/0246; A61F 13/0253; C09J 133/04; C09J 133/066; C09J 133/068; C09J 133/08; C09J 133/10; C09J 133/12; C09J 133/14; C09J 133/20; C09J 133/26; C09J 2433/00; C09J 11/06; C09J 7/38; C09J 2201/20; C09J 2205/102; C09J 2475/00; C09J 2483/00

See application file for complete search history.

(56) References Cited

U.S. PATENT DOCUMENTS

| | | | | |
|---|---|---|---|---|
| 3,645,835 | A * | 2/1972 | Hodgson | A61F 13/023 132/73 |
| 4,331,576 | A * | 5/1982 | Colon et al. | 524/271 |
| 5,124,076 | A * | 6/1992 | Smuckler | 252/519.33 |

(Continued)

OTHER PUBLICATIONS

International Search Report dated Sep. 27, 2013 (PCT/US2013/050237).

*Primary Examiner* — Scott R. Walshon
(74) *Attorney, Agent, or Firm* — Thomas | Horstemeyer, LLP

(57) ABSTRACT

In one embodiment, a selectively-releasable adhesive includes a base adhesive compound and a releasing compound that is blended with the base adhesive compound, the releasing compound being capable of decreasing the adhesive strength of the base adhesive compound when a releasing agent is applied to the selectively-releasable adhesive.

23 Claims, 3 Drawing Sheets

(51) Int. Cl.
    *A61L 15/58*    (2006.01)
    *C09J 7/38*    (2018.01)

(56) References Cited

U.S. PATENT DOCUMENTS

| | | | |
|---|---|---|---|
| 5,352,516 A * | 10/1994 | Therriault et al. | 428/355 CN |
| 5,429,590 A | 7/1995 | Saito et al. | |
| 5,848,966 A * | 12/1998 | Gusakov et al. | 600/372 |
| 6,063,231 A * | 5/2000 | Adler et al. | 156/704 |
| 6,103,951 A | 8/2000 | Freeman | |
| 6,998,432 B2 | 2/2006 | Murkami et al. | |
| 7,056,526 B2 * | 6/2006 | Kuroda | A61K 9/7061 |
| | | | 424/443 |
| 7,745,562 B2 * | 6/2010 | Rosing et al. | 528/272 |
| 7,887,915 B2 * | 2/2011 | Rosing et al. | 428/355 R |
| 8,263,677 B2 * | 9/2012 | Conger | A61K 8/8152 |
| | | | 424/401 |
| 2006/0034905 A1 | 2/2006 | Singh et al. | |
| 2009/0018306 A1 | 1/2009 | Rosing et al. | |
| 2009/0047256 A1 * | 2/2009 | Bettinger et al. | 424/93.7 |
| 2011/0052646 A1 * | 3/2011 | Kaigler, Sr. | 424/400 |
| 2011/0060065 A1 * | 3/2011 | Vu | A61K 8/8152 |
| | | | 521/149 |

\* cited by examiner

SELECTIVELY-RELEASABLE ADHESIVES AND ARTICLES THAT INCORPORATE THEM

CROSS-REFERENCE TO RELATED APPLICATION(S)

This application claims priority to U.S. Provisional Application Ser. No. 61/671,449, filed Jul. 13, 2012, which is hereby incorporated by reference herein in its entirety.

BACKGROUND

Adhesives are used in many applications, including consumer, industrial, and medical applications. Although some adhesives are intended to form a permanent or semi-permanent bond with the objects to which they are applied, many adhesives are used in less permanent applications. The latter type of adhesives are often used in applications in which an article is to be affixed to an object and then later removed. An example is the common adhesive bandage strip, which is intended to stick to the skin until the wearer wishes to remove the bandage strip.

A problem with the adhesives that are used in temporary applications is that the adhesive may still adhere well to an object to which it has been applied when the time for removal has arrived. For example, in the case of an adhesive bandage strip, such adhesion can make it more difficult to remove the bandage strip and therefore may cause discomfort to the wearer. Although such discomfort may be relatively mild, the discomfort from removal of other types of bandages can be much greater. For example, removal of an adhesive medical dressing or medical tape that secures a non-adhesive dressing to the skin of a geriatric or pediatric patient can not only cause the patient a great deal of pain, but further cause skin tissue damage. Moreover, the stronger the adhesion to the skin of the patient, the greater the pain and/or tissue damage.

BRIEF DESCRIPTION OF THE DRAWINGS

The disclosed adhesives and articles can be better understood with reference to the following drawings. The components in the drawings are not necessarily to scale.

DETAILED DESCRIPTION

Figure 1:
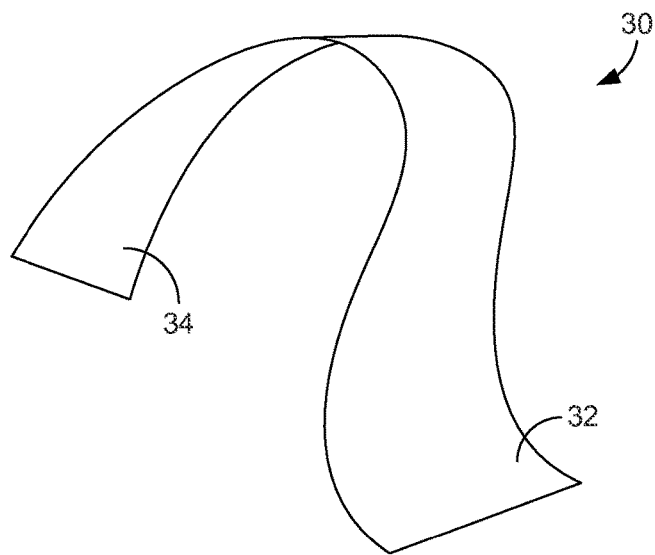
FIG. 1 is a perspective view of an embodiment of adhesive tape that incorporates a selectively-releasable adhesive.

As described above, it can be difficult to remove articles that have been affixed to objects using conventional adhesives. Moreover, in cases in which the article is a medical article, such as bandage, and the object is a patient, pain and/or tissue damage can occur from such removal. Described herein are adhesives that lose much of their adhesive strength when a releasing agent is applied to the adhesive. Therefore, such adhesives can be used in applications in which selective release of the adhesive (i.e., selective loss of peel strength) is desired. In some embodiments, the adhesive comprises a base adhesive compound that is blended with a releasing compound. When the releasing agent is applied to the adhesive, the releasing compound is activated and dramatically reduces the adhesive strength of the adhesive. In cases in which the adhesive article is a bandage or medical tape, the article can then be easily removed without causing significant pain or tissue damage, and without leaving significant residue behind.

In the following disclosure, various embodiments of adhesives and adhesive articles are described. Although specific embodiments are presented, those embodiments are mere example implementations and, therefore, other embodiments are possible. All such embodiments are intended to fall within the scope of this disclosure.

Adhesive Compound Synthesis and Characteristics

As identified above, the selectively-releasable adhesives of this disclosure generally comprise a base adhesive compound that is blended with a releasing compound that, when activated by a suitable releasing agent, dramatically reduces the adhesive strength of the adhesive. In some embodiments, the base adhesive compound comprises an acrylic polymer adhesive. In other embodiments, the base adhesive compound comprises a different adhesive, such as silicone adhesive, rubber adhesive, polyurethane adhesive, or hydrocolloid blended with an adhesive such as polyisobutylene or styrene-soprene-styrene. In cases in which the base adhesive compound is an acrylic polymer adhesive, the adhesive compound is made from the polymerization of acrylic acid with variations in the chemical composition designed to balance internal cohesion or shear as well as tack and peel strength. Irrespective of its composition, the base adhesive compound provides the adhesive strength to the adhesive that enables it to stick to objects, including human skin.

In some embodiments, the releasing compound comprises a prepolymer formed from a multifunctional alcohol and a multifunctional carboxylic acid. The term "multifunctional alcohol" refers to any alcohol that has two or more hydroxyl (—OH) groups, while the term "multifunctional carboxylic acid" refers to any carboxylic acid that has two or more acid (—COOH) groups. Example multifunctional alcohols include glycerol, monomeric carbohydrates such as glucose and mannose, and small polyols such as oligo(vinyl alcohol). Example multifunctional carboxylic acids include diacids such as sebacic acid, succinic acid, oxalic acid, and malic acid, and triacids such as citric acid. In some embodiments, the releasing compound of the adhesive comprises a prepolymer comprising a mixture of glycol and sebacic acid, referred to herein as oligo(glycerol-sebacate) or OGS. An example of synthesis of OGS is described in the following several paragraphs.

Highly-purified sebacic acid can be used to prepare the OGS. In some embodiments, sebacic acid can be rigorously purified by combining a relatively small amount of sebacic acid with a relatively large amount of ethanol and heating the mixture until the sebacic acid completely dissolves. Once the sebacic acid has dissolved, the hot sebacic acid solution can be filtered under a vacuum and the filtrate can be refrigerated for several hours to enable crystallization. The sebacic acid crystals can then be collected and intermittently filtered under vacuum to collect the crystals. After the completion of the filtration, the above process (dissolution, crystallization, and filtration) can be repeated multiple times (e.g., 3-4 times) to ensure a high level of purification.

Thereafter, the air-dried sebacic acid crystals can be heated under a vacuum to remove any residual ethanol or moisture.

OGS can be formed by mixing the sebacic acid with the glycerol to form the prepolymer. As used herein, the term "prepolymer" describes an uncured polymeric mixture that exhibits little or no crosslinking. As a result, OGS has a crosslink density significantly less than 1%. By way of example, the OGS has a crosslink density of 0 to approximately 0.05%. In some embodiments, the OGS mixture can be prepared by mixing glycerol and sebacic acid at a molar ratio of approximately 0.5 to 1.5 glycerol to 1 sebacic acid, heating the mixture at an elevated temperature of approximately 120 to 150° C. until water is generated under nitrogen atmosphere, and maintaining the reaction at the elevated temperature as the pressure is reduced until an approximately 0.5 to 2 molar equivalent of water is removed from the mixture. In some embodiments, the reaction can be performed under a vacuum of approximately 1 to 5 Torr. The OGS can then be permitted to cool and solidify.

The selectively-releasable adhesive can be formed by blending the releasing compound with the base adhesive compound. In some embodiments, the base adhesive compound comprises approximately 50 to 95 percent weight (w/w %) of the blended material and the releasing compound comprises approximately 5 to 50 w/w % of the material. By way of example, the blended prepolymer can be an approximately 95/5, 90/10, 85/15, 80/20, or 70/30 blend of base adhesive compound and releasing compound. Notably, other components, such as one or more drugs, can be added to the blended prepolymer, if desired.

When the releasing compound is a solid at room temperature, as is the case for OGS, it can be melted or dissolved with a solvent to facilitate blending with the base adhesive compound. In the former case, the releasing compound can be melted at a temperature of approximately 40 to 60° C. In the latter case, the solvent can, in some embodiments, be a polar organic solvent. Example solvents include ethyl acetate, ethanol, and tetrahydrofuran. In some embodiments, the solvent can be added to the releasing compound in a concentration of approximately 10 to 90 w/w %. Solvent can also be added to the base adhesive compound to reduce its viscosity and facilitate blending with the releasing compound. In some embodiments, the solvent used with the releasing compound can be mixed with the base adhesive compound prior to its mixing with the releasing compound. In some embodiments, the solvent can be added to the base adhesive compound in a concentration of approximately 33 to 67 w/w %. By way of example, the solvent can be added to the base adhesive compound in a concentration of approximately 45 to 55 w/w %.

In cases in which one or more solvents are used to facilitate blending of the base adhesive compound and/or the releasing compound, the solvent(s) can be evaporated from the blend to produce the selectively-releasable adhesive. In some embodiments, the blend is applied to a substrate (see below) and is heated at a temperature of approximately 140 to 280° F. for approximately 3 to 10 minutes to evaporate the solvent. Notably, these temperatures and durations are not great enough to cause significant crosslinking within the OGS. Indeed, to achieve even light crosslinking, the OGS would need to be exposed to an elevated temperature for many hours. The resulting selectively-releasable adhesive is highly tacky and typically sticks well to both inanimate objects and living tissue, such as skin.

In cases in which the selectively-releasable adhesive is applied to a substrate, the adhesive blend can be applied to the substrate prior to evaporation of the solvent. For example, the adhesive blend can be applied to the substrate so as to have a thickness of approximately 1.9 to 2.4 grams per 100 square inches. The coated substrate can then be passed through an oven to evaporate the bulk of the solvent, and the substrate can be wound up to form a roll of material that can be stored for later processing. Irrespective of the nature of the article to be produced, further processing can include perforation of the coated substrate so as to form passages through which an appropriate releasing agent can pass to reach the interface between the adhesive article and the object to which the article is applied (e.g., skin surface).

Selective Release

As mentioned above, the adhesive strength of the disclosed adhesive can be selectively reduced through the application of a releasing agent. Suitable releasing agents include alcohols, such as ethanol, 1-propanol, 2-propanol, and 1-butanol; ketones, such as acetone, and methyl ethyl ketone; ethers, such as tetrahydrofuran and diethyl ether; amides, such as N,N-dimethyl foramide; sulfoxides, such as dimethyl sulfoxide; and esters, such as ethyl acetate. In some embodiments, the releasing agent can be a mixture of one or more of the above compounds and water. For example, a suitable releasing agent can be a solution of approximately 50 to 95 w/w % alcohol and approximately 5 to 50 w/w % water.

The mechanism with which adhesive strength is reduced may relate to swelling of the releasing compound within the adhesive. Specifically, when the releasing agent is absorbed by the releasing compound (e.g., OGS), it swells and may break the adhesive bonds formed between the base adhesive compound (e.g., acrylic polymer adhesive) and the object to which it has been adhered. Accordingly, the releasing compound can be said to be "activated" by the releasing agent. Once the releasing agent evaporates, however, the releasing compound shrinks and the adhesive strength of the adhesive returns.

The releasing agent can be applied in a variety of ways. In some embodiments, the releasing agent can be sprayed onto the adhesive or the adhesive article. In other embodiments, the releasing agent can be applied using an applicator, such as a sponge-tip applicator.

Example Applications

The selectively-releasable adhesives described above can be used in various applications, including consumer, industrial, and medical applications. Described in the following are a few examples of such applications.

FIG. 1 illustrates an embodiment of adhesive tape 30 that incorporates a selectively-releasable adhesive. By way of example, the tape 30 can be used in medical applications to secure bandages or other articles to a patient and therefore adheres to the patient's skin. The tape 30 generally comprises a continuous, thin, and flexible strip having an outer side 32 and an inner side 34.

Figure 2:
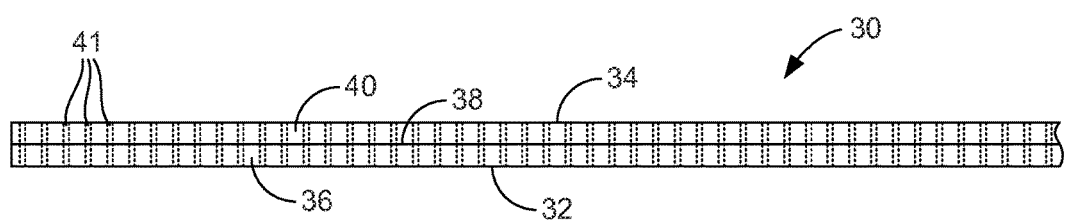
FIG. 2 is a side view of the adhesive tape of FIG. 1.

FIG. 2 illustrates an example construction that can be used to form the tape 30 shown in FIG. 1. In the embodiment of FIG. 2, the tape 30 includes a substrate 36 having an inner surface 38 to which has been applied an adhesive layer 40 that comprises the above-described selectively-releasable adhesive. In some embodiments, the substrate 36 comprises a flexible material that is adapted to conform to the contours of subjects to which the tape 30 is applied. Example constructions for the substrate 36 include one or more layers of paper, textile, polymer, foam, or foil. Example textiles include woven and nonwoven fabrics that are made of natural and/or manmade fibers. Example polymers include polyurethane, polypropylene, polyethylene, and polyvinyl chloride. By way of example, the adhesive layer 40 is approximately 10 to 200 µm thick.

In some embodiments, the substrate 36 and adhesive layer 40 are porous or perforated so that a releasing agent applied to the outer side 32 of the tape 30 (i.e., outer surface of the substrate) can reach the inner side 34 of the tape (i.e., outer surface of the adhesive) at the skin-tape interface to facilitate release. As shown in FIG. 2, the perforations 41 can form passages that extend from the outer side 32 to the inner side 34 of the tape 30. In some embodiments, the perforations 41 can be approximately 200 to 800 µm wide (e.g., in diameter) and the tape 30 can be have a perforation density of approximately 5 to 500 perforations per square inch. For example, the perforations 41 can have a density of approximately 30 perforations per square inch. In other embodiments, the substrate 36 and adhesive layer 40 are not porous or perforated but releasing agent can be applied to the edges of the substrate to facilitate release.

Figure 3:
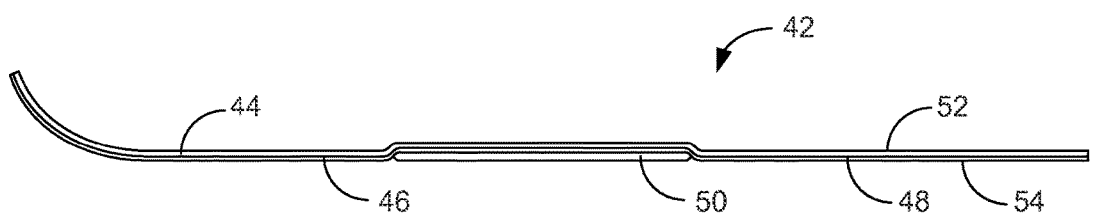
FIG. 3 is a side view of an embodiment of an adhesive bandage strip that incorporates a selectively-releasable adhesive.

FIG. 3 illustrates a medical dressing in the form of an adhesive bandage strip 42 that also incorporates the selectively-releasable adhesive. As indicated in FIG. 3, the bandage strip 42 includes a substrate 44 having an inner surface 46 to which has been applied an adhesive layer 48 that comprises the above-described selectively-releasable adhesive. The substrate 44 can comprise a flexible material that has a construction similar to the substrate 36 described above. The substrate 44 and adhesive layer 48 can likewise be porous or perforated so that a releasing agent applied to the outer side 52 of the bandage strip 42 (i.e., outer surface of the substrate) can reach the inner side 54 of the bandage strip (i.e., outer surface of the adhesive layer) at the skin-bandage interface to facilitate release. As with the tape 30, the perforations can be approximately 200 to 800 µm wide (e.g., in diameter) and can be present in a density of approximately 5 to 500 perforations per square inch. As is further indicated in FIG. 3, the bandage strip 42 can include a central dressing element 50 designed to overlie a cut or other wound. In some embodiments, the dressing element 50 can include medications that facilitate wound healing or pharmaceutical drugs.

Figure 4:
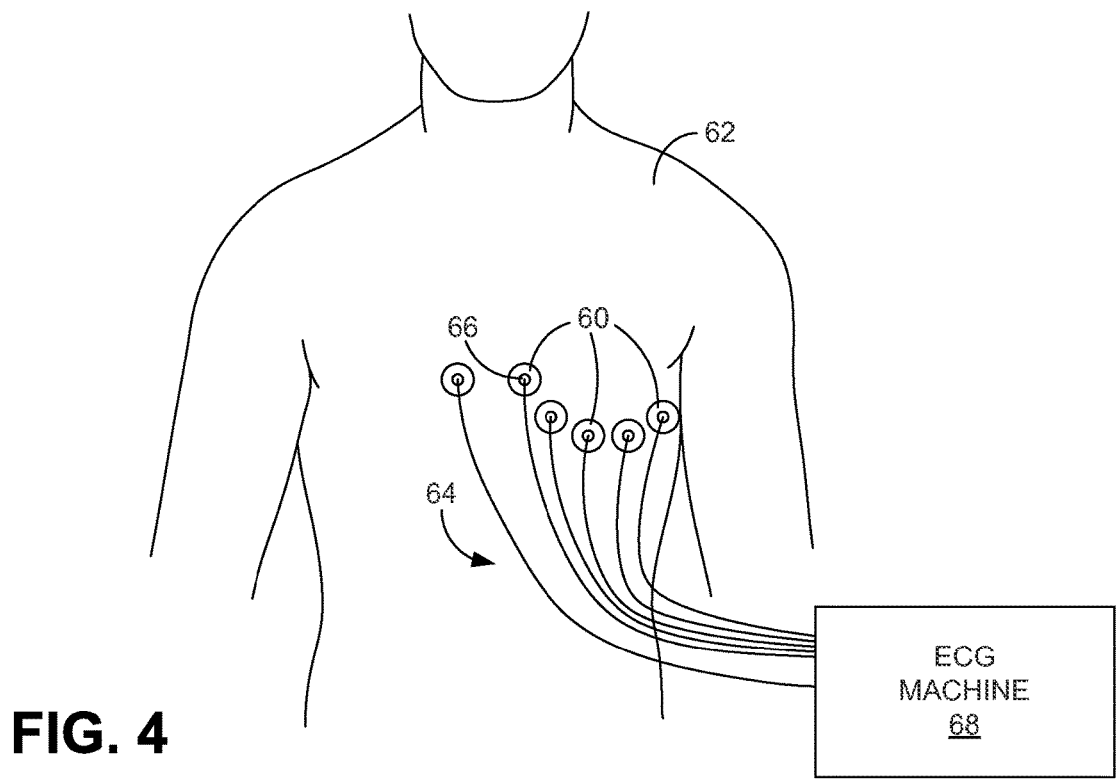
FIG. 4 is a front view of a patient to which adhesive ECG leads that incorporate a selectively-releasable adhesive have been applied.
Figure 5:
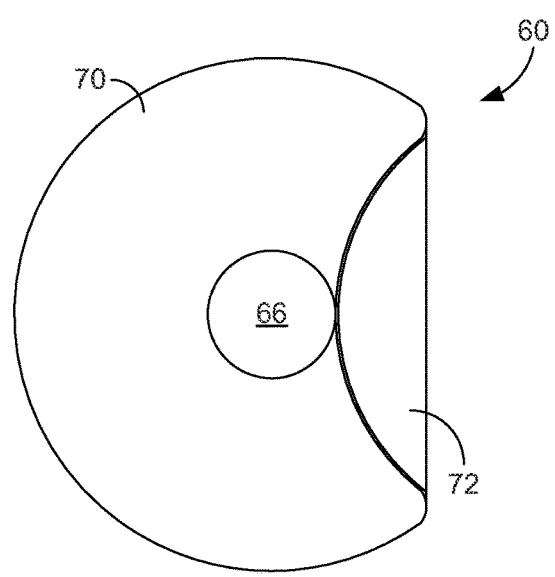
FIG. 5 is a top view of an embodiment of an ECG lead shown in FIG. 4.

There are various other applications for the selectively-releasable adhesive beyond adhesive tape and bandages. FIG. 4 illustrates one example of such an application. Specifically, illustrated in FIG. 4 are multiple adhesive electrocardiogram (ECG) leads 60 that have been applied to a patient 62. As indicated in the figure, wires 64 extend from electrodes 66 provided on the leads 60 to an ECG machine 68. FIG. 5 illustrates an example configuration for one of the ECG leads 60. As indicated in FIG. 5, the ECG lead 60 comprises a substrate 70 to which is applied to an adhesive layer 72 that comprises the selectively-releasable adhesive. As with the tape 30 and the adhesive bandage strip 42, the substrate 70 and its adhesive layer 72 can be porous to facilitate release of the adhesive.

Figure 6:
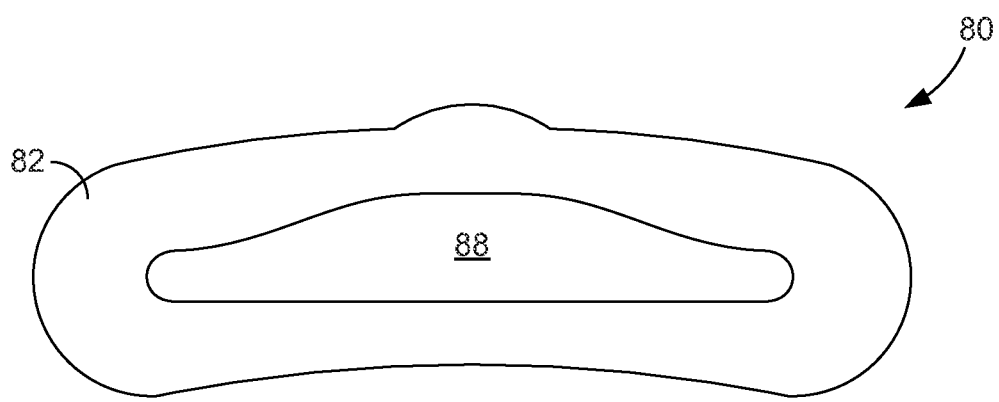
FIG. 6 is a top view of an embodiment of a nasal dilator strip.
Figure 7:
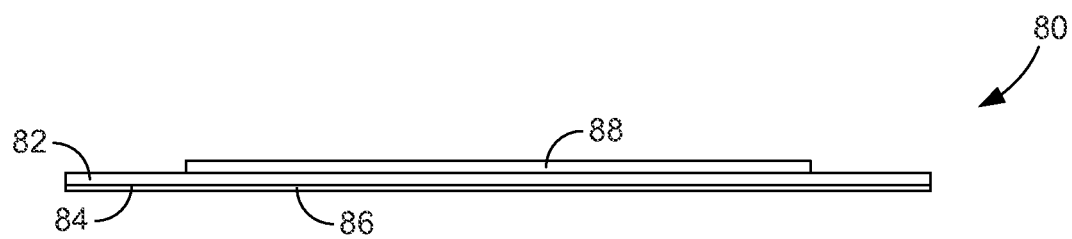
FIG. 7 is a side view of the nasal dilator strip of FIG. 6.

In a further application, the selectively-releasable adhesive can be provided on a nasal dilator strip of the type that is adhered to the skin across the bridge of the nose. In order to make such a strip stay in place on the nose, high strength adhesives are typically needed. Unfortunately, it can be difficult to remove such strips after they are no longer needed due to that high strength. When a selectively-releasable adhesive is used, however, both high strength and easy release can be achieved. FIGS. 6 and 7 illustrate an example nasal dilator strip 80. As shown in these figures, the nasal dilator strip 80 comprises a substrate 82 having an inner surface 84 to which a layer of selectively-releasable adhesive 86 is applied. In addition, the dilator strip 80 includes a resilient element 88 that expands the nasal passages once the strip has been affixed to the bridge of the nose. As with the other articles, the substrate 82 and adhesive layer 86 can be porous or perforated to facilitate release.

In yet other applications, the selectively-releasable adhesive can be provided on epidermal patches and intravenous (IV) fixation wound dressings.

The invention claimed is:

1. A selectively-releasable adhesive comprising:
   a base adhesive compound; and
   a releasing compound that is blended with the base adhesive compound, the releasing compound being capable of decreasing the adhesive strength of the base adhesive compound when a releasing agent is applied to the selectively-releasable adhesive, wherein the releasing compound is an uncured prepolymer formed from a multifunctional alcohol and a multifunctional carboxylic acid.

2. The selectively-releasable adhesive of claim 1, wherein the base adhesive compound comprises approximately 50 to 95 percent weight of the selectively-releasable adhesive and the releasing compound comprises approximately 5 to 50 percent weight of the selectively-releasable adhesive.

3. The selectively-releasable adhesive of claim 1, wherein the base adhesive compound comprises approximately 80 to 90 percent weight of the selectively-releasable adhesive and the releasing compound comprises approximately 20 to 10 percent weight of the selectively-releasable adhesive.

4. The selectively-releasable adhesive of claim 1, wherein the base adhesive compound is an acrylic polymer adhesive, a silicone adhesive, a rubber adhesive, a polyurethane adhesive, a hydrocolloid blended with an adhesive, or a mixture thereof.

5. The selectively-releasable adhesive of claim 1, wherein the base adhesive compound is an acrylic polymer adhesive.

6. The selectively-releasable adhesive of claim 1, wherein the multifunctional alcohol is selected from the group consisting of glycerol, monomeric carbohydrates, small polyols, and combinations thereof.

7. The selectively-releasable adhesive of claim 1, wherein the multifunctional carboxylic acid is selected from the group consisting of diacids, triacids, and mixtures thereof.

8. The selectively-releasable adhesive of claim 1, wherein the releasing compound comprises oligo(glycerol-sebacate).

9. The selectively-releasable adhesive of claim 1, wherein the releasing compound is capable of decreasing the adhesive strength of the base adhesive compound when one or more of an alcohol, ether, amide, or ester solution is applied to the selectively-releasable adhesive.

10. The selectively-releasable adhesive of claim 1, wherein the releasing compound is water-insoluble.

11. An adhesive article comprising:
    a substrate; and
    an adhesive layer applied to the substrate, the adhesive layer comprising a selectively-releasable adhesive having a blend of a base adhesive compound and a releasing compound, the releasing compound being capable of decreasing the adhesive strength of the base adhesive compound when a releasing agent is applied to the adhesive layer, wherein the releasing compound is an uncured prepolymer formed from a multifunctional alcohol and a multifunctional carboxylic acid.

12. The adhesive article of claim 11, wherein the base adhesive compound comprises approximately 50 to 95 percent weight of the selectively-releasable adhesive and the releasing compound comprises approximately 5 to 50 percent weight of the selectively-releasable adhesive.

13. The adhesive article of claim 11, wherein the base adhesive compound is an acrylic polymer adhesive.

14. The adhesive article of claim 11, wherein the multifunctional alcohol is selected from the group consisting of glycerol, monomeric carbohydrates, small polyols, and combinations thereof.

15. The adhesive article of claim 11, wherein the multifunctional carboxylic acid is selected from the group consisting of diacids, triacids, and mixtures thereof.

16. The adhesive article of claim 11, wherein the releasing compound comprises oligo(glycerol-sebacate).

17. The adhesive article of claim 11, wherein the substrate comprises one or more layers of paper, textile, polymer, foam, or foil.

18. The adhesive article of claim 11, wherein the substrate and adhesive layer are perforated.

19. The adhesive article of claim 18, wherein the perforations extend from an outer side to an inner side of the article so as to enable the releasing agent to pass from the outer side of the article to an interface at which the article contacts an object to which it is adhered.

20. The adhesive article of claim 11, wherein the article is medical tape.

21. The adhesive article of claim 11, wherein the article is a medical dressing.

22. The adhesive article of claim 11, wherein the article is an adhesive bandage strip.

23. The adhesive article of claim 11, wherein the releasing compound is water-insoluble.

\* \* \* \* \*